United States Patent [19]

Young et al.

[11] Patent Number: 5,022,912

[45] Date of Patent: * Jun. 11, 1991

[54] METHODS FOR FERTILIZING WITH AMMONIACAL FERTILIZERS

[75] Inventors: Donald C. Young, Fullerton; James A. Green, II, Chino, both of Calif.

[73] Assignee: Union Oil Company of California, Los Angeles, Calif.

[ * ] Notice: The portion of the term of this patent subsequent to Feb. 23, 2005 has been disclaimed.

[21] Appl. No.: 128,146

[22] Filed: Dec. 3, 1987

Related U.S. Application Data

[63] Continuation-in-part of Ser. No. 685,454, Nov. 16, 1984, Pat. No. 4,476,113, and Ser. No. 931,517, Nov. 17, 1986, abandoned, said Ser. No. 685,454, is a continuation-in-part of Ser. No. 315,492, Oct. 27, 1981, Pat. No. 4,476,113, and Ser. No. 490,461, May 2, 1983, abandoned.

[51] Int. Cl.$^5$ .............................................. C05C 9/00
[52] U.S. Cl. ......................................... 71/30; 71/902; 71/903; 71/63; 424/701
[58] Field of Search ...................... 71/28, 30, 63, 902, 71/903; 424/161

[56] References Cited

U.S. PATENT DOCUMENTS

| | | |
|---|---|---|
| 1,044,452 | 3/1912 | Halland . |
| 1,772,511 | 8/1930 | Hartzell et al. ................... 424/161 |
| 2,046,128 | 6/1936 | McQuiston . |
| 2,676,129 | 8/1954 | Bashour . |
| 2,731,487 | 1/1956 | Bashour . |
| 2,836,532 | 5/1958 | Seifter ............................. 424/162 |
| 2,836,533 | 5/1958 | Seifter . |
| 3,133,857 | 5/1964 | Sweezey . |
| 3,797,738 | 3/1974 | Fitzhugh ........................... 47/48.5 |
| 3,837,304 | 9/1974 | Carroll . |
| 4,042,501 | 8/1977 | Thompson . |
| 4,078,912 | 3/1978 | Hawkins .............................. 71/28 |
| 4,214,888 | 7/1980 | Young ................................ 71/28 |
| 4,435,304 | 3/1984 | Lindstrom et al. ................ 252/156 |
| 4,726,144 | 2/1988 | Young et al. ....................... 47/58 |

FOREIGN PATENT DOCUMENTS 1501516 5/1975 United Kingdom .

OTHER PUBLICATIONS

C. R. Acad. Sci., Paris, pp. 951-952, Zins et al.
J. Sci. Fd. Agric., 1977, 28, 673-683, Inhibition of Nitrification of Nitrapyrin, Carbon Disulphide and Trithiocarbonate, by John Ashworth, Geoffrey G. Briggs, Avis A. Evans and Jiri Matula.
Zins et al., Compt. Rend. (C), 276 (1973), 951-954; Chemical Abstracts, 78, 143265m (1973).
"The Soil Pest Complex," *Agricultural and Food Chemistry*, vol. 3, pp. 202-205 (1955).
*Journal of the Chemical Society*, O'Donoghue and Kahan, vol. 89 (II), pp. 1812-1818 (1906).
*Journal of the Chemical Society*, Yeoman, vol. 119, pp. 38-54 (1921).
*Journal of the Chemical Society*, Mills and Robinson, vol. 1928 (II), pp. 2326-2332 (1928).
*Soil Biology and Biochemistry*, Bremner and Bundy, vol. 6, pp. 161-165 (1974).
*Chemistry and Industry*, Ashworth et al., Sep. 6, 1975, pp. 749-750.
*Agricultural Chemicals*, Book III, "Miscellaneous Chemicals," W. T. Thomson, 1976-1977 Revision, (Thomson Publications, P.O. Box 7964, Fresno, CA), pp. 11-12 (1978).
*Agricultural Chemicals*, Book IV, "Fungicides," W. T. Thomas, 1976-1977 Revision, (Thomson Publications, P.O. Box 7964, Fresno, CA), pp. 15-16 (1976).

*Primary Examiner*—Peter F. Kulkosky
*Attorney, Agent, or Firm*—Gregory F. Wirzbicki; Michael H. Laird

[57] ABSTRACT

The invention is directed to the fumigation of soils, enclosed spaces, agricultural products and other commodities, etc., using compositions which decompose to form carbon disulfide and certain other biocidal materials. Such fumigation can be used to control bacteria, fungi, insects, nematodes, rodents, nitrification, and weeds.

Fumigant compositions are described herein as "thiocarbonates," including, without limitation, salts of trithiocarbonic acid and tetrathiocarbonic acid, compositions having empirical formulae intermediate to these acids salts (such as $MCS_{3.7}$, wherein M is a divalent metal ion), and compositions containing substances in addition to thiocarbonates, such as a stabilized ammonium tetrathiocarbonate which contains ammonium sulfide, i.e., $(NH_4)_2CS_4(NH_4)_2S$.

The compositions are generally water soluble and can be prepared, stored, and used in aqueous solutions. Thiocarbonate solutions of the invention are stable during prolonged periods of storage in a closed container, exhibit a low vapor pressure, and are not flammable. For soil fumigation, thiocarbonates can be mixed with fertilizers to provide a multi-functional application.

16 Claims, No Drawings

METHODS FOR FERTILIZING WITH AMMONIACAL FERTILIZERS

CROSS REFERENCE TO RELATED APPLICATIONS

This application is a continuation-in-part of our copending application Ser. No. 685,454 filed Nov. 16, 1984, for FUMIGATION METHODS AND COMPOSITIONS, now U.S. Pat. No. 4,726,114, and of our copending application Ser. No. 931,517 filed Nov. 17, 1986, for FUMIGATION METHODS, said application Ser. No. 685,454 being a continuation in part of Ser. No. 06/315,492, filed Oct. 27, 1981 for Stabilized Fumigant Compositions, now U.S. Pat. No. 4,476,113 and a continuation in part of Ser. No. 06/490,461, filed May 2, 1983 for Method of Fumigation, now abandoned.

TECHNICAL FIELD

The invention relates to the field of agriculture. More specifically, the invention pertains to the fumigation of soils, enclosed spaces, and agricultural commodities.

INTRODUCTION

Among the more economically serious plant parasites are nematodes, which are roundworms, comprising as many as 10,000 species, of which at least 150 are known to adversely affect plant life. Plant parasitic nematodes have been known since about the year 1750. Most of the nematodes which cause crop damage do so by feeding on plant roots, and therefore are found primarily in the upper few inches of soil in the roots or in close proximity to the roots. Nematode feeding causes hypertrophy or gall formation, and the evidence of heavy infestation is plant stunting, pale foliage, wilting, and even plant death in extreme cases.

Virtually all of the world's crops and ornamental plants can be attacked by parasitic nematodes. Important destructive nematode species include the root knot nematodes which are hosted by tomatoes, alfalfa, cotton, corn, potatoes, citrus and many other crops, the golden nematode of potatoes, the sugar beet cyst nematode and the citrus nematode. These, and a few other species, are described in "The Soil Pest Complex", *Agricultural and Food Chemistry*, Vol. 3, pages 202–205 (1955). Also described therein is a further complication resulting from nematode infestation, namely a lowered resistance to the effects of plant attack by bacteria and pathogenic soil fungi.

Except for small volumes of soil which can be sterilized, it has not been found possible to eliminate nematodes. Parasite populations can, however, be kept at levels which economically permit agricultural operations by soil fumigation, crop rotation using non-hosting plant varieties, and (to a much lesser extent) the development of plants which are resistant to infestation. In many instances, control of nematodes is achieved only by combinations of these techniques, and most control programs have proven quite costly.

Another serious problem in agriculture is the attack of plants by pathogenic microorganisms, particularly fungi. Such pathogens are normally controlled by fumigation, prior to crop planting, using broad spectrum biocides, many of which are no longer regarded as environmentally safe. Certain narrow spectrum fungicides are available, but are extremely expensive and lose effectiveness against successive generations of fungi, due to genetic adaptability.

Carbon disulfide is the first reported soil fumigant, used in Europe during the 1870's to control the sugar beet nematode. This agent is commercially impractical, however, since very large quantities must be applied, due to its high volatility. Further, the material is quite flammable, reportedly being ignited even by static electricity resulting from pouring the material out of drums. In addition, carbon disulfide possesses a very objectionable odor, and its vapors are toxic to humans. When sold for fumigant use, the carbon disulfide is normally mixed with an inert fire retarding compound, such as carbon tetrachloride, and occasionally also with another fumigant. Typically, these compositions do not contain over about 20 percent by weight of carbon disulfide.

In addition to soil uses, carbon disulfide has been proven effective in the fumigation of commodities, as an insecticide, as a rodenticide, and for controlling certain weeds.

Numerous compositions possessing nematocidal properties have been developed, including active ingredients such as the polyamines of U.S. Pat. No. 2,979,434 to Santmyer, the heterocyclic compounds of U.S. Pat. No. 2,086,907 to Hessel, and various halogenated compounds. Among the useful halogen-containing nematocides are 1,2-dibromoethane, methyl bromide, 3-bromopropyne, 1,2-dichloropropane, ethylene dichloride and others, all of which are quite phytotoxic, therefore restricting their utility to mostly preplant treatments.

One compound which enjoyed considerable commercial success is 1,2-dibromo-3-chloropropane (DBCP), which can be used to control nematodes in soils with growing perennial plants. However, use of this material has been limited due to a finding of undesirable reproductive system effects in workers exposed to the chemical, and the possibility that the compound is a carcinogen. The unavailability of DBCP has been a serious setback to growers of perennial crops, such as grapes, stone fruits and nuts, since these crops experience more severe cumulative nematode population increases, and most replacement soil fumigants are phytotoxic. U.S. Pat. Nos. concerned with the use of DBCP as a soil fumigant include 2,937,936 to Schmidt and 3,049,472 to Swezey.

A further class of materials used to control nematodes includes some thiocarbonates. U.S. Pat. No. 2,676,129 to Bashour describes the preparation of lower aliphatic disubstituted trithiocarbonates having the structure as in (1):

wherein R and $R_2$ are alkyl radicals having from three to nine carbon atoms. The compounds were dissolved in acetone and added to nematode-infested coils, resulting in control of the nematodes.

Other compounds have been reported by Seifter in U.S. Pat. Nos. 2,836,532 and 2,836,533, the former relating to the use of sodium and potassium trithiocarbonate, and the latter pertaining to alkali metal and ammonium salts of tetrathioperoxycarbonic acid. Both are described as effective in nematode control.

These references state that "not all carbon disulfide derivatives are effective nematode toxicants." Furthermore, U.S. Pat. No. 2,836,532 points out that sodium trithiocarbonate is unexpectedly superior to potassium trithiocarbonate as a nematocide.

The chemistry of thiocarbonic acids and salts has been studied in some detail, as indicated in the papers by O'Donoghue and Kahan, *Journal of the Chemical Society*, Vol. 89 (II), pages 1812-1818 (1906); Yeoman, *Journal of the Chemical Society*, Vol. 119, pages 38-54 (1921); and Mills and Robinson, *Journal of the Chemical Society*, Vol. 1928 (II), pages 2326-2332 (1928). According to O'Donoghue and Kahan, derivatives of thiocarbonic acid were prepared by Berzelius, who reacted aqueous solutions of hydrosulfides with carbon disulfide, the reactions occurring as in (1):

$$2 KHS + CS_2 \rightarrow K_2CS_3 + H_2S \tag{1}$$

giving unstable solutions which yielded unstable crystalline salts.

Other thiocarbonates were prepared and further characterized by O'Donoghue and Kahan. Their paper, at page 1818, reports the formation of ammonium thiocarbonate by reacting liquid ammonia with cold alcoholic thiocarbonic acid, prepared by dropping a solution of "calcium thiocarbonate" into concentrated hydrochloric acid. The "calcium thiocarbonate" utilized by the authors is described as a double salt, including the calcium cation in combination with both hydroxide and trithiocarbonate anions.

The noted paper by Yeoman reports the further study of thiocarbonates (called trithiocarbonates therein) and also reports the preparation and properties of perthiocarbonates (or tetrathiocarbonates), derivatives of tetrathiocarbonic acid, $H_2CS_4$. Yeoman prepared ammonium trithiocarbonate by saturating an alcoholic ammonia solution with hydrogen sulfide, and then adding carbon disulfide; dry ether was added to precipitate the product salt. Ammonium perthiocarbonate was prepared in a similar manner, except that after reacting the ammonia and hydrogen sulfide, elemental sulfur was added to form the disulfide, $(NH_4)_2S_2$; adding carbon disulfide immediately precipitated the product.

Yeoman states that "solutions of both ammonium trithiocarbonate and perthiocarbonate are very unstable" due to both decomposition to form thiocyanate as a product, and to "complete dissociation into ammonia, hydrogen sulfide, and carbon disulfide."

Considerable explanation is provided concerning the stability of thiocarbonates, as exemplified by sodium trithiocarbonate and perthiocarbonate. Sodium trithiocarbonate solutions in water are said to remain stable only if oxygen and carbon dioxide are "rigidly excluded"; the presence of oxygen causes decomposition to form carbon disulfide and thiosulfates, while carbon dioxide decomposes the solution to give a carbonate and carbon disulfide. Similarly, solutions of sodium perthiocarbonate are reported to be stable for a considerable time in the absence of oxygen, the presence of air causing decomposition into thiosulfate and carbon disulfide, while carbon dioxide decomposes the compound to form a carbonate, elemental sulfur, carbon disulfide, and hydrogen sulfide. The potassium thiocarbonates behave similarly, according to Yeoman.

Yeoman also attempted to prepare and characterize the stability of thiocarbonate salts of four of the alkaline earth metals. Yeoman was unable to prepare a "pure" calcium tri- or tetrathiocarbonate, but observed that the double salt of calcium trithiocarbonate that he prepared was more stable (probably because it was less hygroscopic) than the sodium or potassium thiocarbonates. The barium tetrathiocarbonate could not be isolated, although Yeoman believed that it existed in solution. Barium trithiocarbonate was found to be stable, although it was alleged to behave like sodium trithiocarbonate when dissolved in water. The preparation of aqueous solutions of the tri- and tetrathiocarbonate of magnesium and strontium was alleged, but the magnesium thiocarbonates were not characterized. However, the stability of none of the magnesium or strontium salts or solutions was determined.

The previously noted paper by Mills and Robinson discusses the preparation of ammonium thiocarbonate by digesting ammonium pentasulfide (obtained by suspending sulfur in aqueous ammonia, then saturating with hydrogen sulfide) with carbon disulfide. A crystalline residue from this digestion was found to be ammonium perthiocarbonate. These authors prepared a "better" ammonium perthiocarbonate product, however, by extracting the ammonium pentasulfide with carbon disulfide in a Soxhlet apparatus.

Another serious problem in agriculture is that of low nitrogen use-efficiency, since crops have been found to recover only 30 to 70 percent of the total amount of expensive fertilizer nitrogen which is applied to the soil. Most of the lost nitrogen is due to nitrite and nitrate ions, which are exceptionally mobile in a soil environment, and therefore are readily lost by surface runoff and also by leaching from the plant root zone into deeper soil. Other losses of these ions are due to denitrification, which is reduction to elemental nitrogen or gaseous nitrogen oxides under conditions of limited aeration. In addition to the direct economic losses, these nitrogen forms constitute environmental pollutants when runoff enters surface and ground water systems.

Although some nitrogen is applied to soil in the form of nitrate (e.g., ammonium nitrate-containing fertilizers), most nitrogen fertilization is with ammonia, ammonium compounds other than nitrate and urea materials. Ammonium nitrogen is fairly tightly bound by various physical and chemical processes in a soil environment and, therefore, is much less subject to losses. Unfortunately, the bound ammonium nitrogen is also less available to plants.

The process of nitrification results in conversion of ammonium ions into nitrate ions. Microbial species known as nitrosomonas oxidize ammonium to nitrate; nitrobacter species oxidize nitrite to nitrate. This more mobile ion is easily taken up by plant roots and is also readily assimilated by plant. In this regard, the nitrification process is desirable, but control of the rate at which conversion occurs has not been easily obtained. Inhibition of nitrification would tend to make the applied nitrogen available to plants over a longer period of time, resulting in an increased plant uptake efficiency.

Various compositions have been offered as inhibitors of nitrification, including expensive organic materials such as 2-chloro-6-(trichloromethyl)-pyridine, 2-amino-4-chloro-6-methyl-pyrimidine, sulfathiazoles, alkanolysulfathiazoles, and others. A paper by J. M. Bremner and L. G. Bundy in *Soil Biology and Biochemistry*, Vol. 6, pages 161-165 (1974) describes the efficacy of various volatile organic sulfur compounds, including methyl mercaptan, dimethyl sulfide, dimethyl disulfide, carbon disulfide, and hydrogen sulfide. Carbon disulfide in very small amounts is described as having "a remarkable inhibitory effect on nitrification of ammonium in soils incubated in closed systems." Carbon disulfide was tested in the field by J. Ashworth et al., *Chemistry and Industry*, Sept. 6, 1975, pages 749–750, and found to be effective as a nitrification inhibitor. Hawkins, in U.S. Pat. No. 4,078,912, describes the use of sodium, potassium and ammonium trithiocarbonates, and of xanthates, either alone or in fertilizer mixtures, to inhibit nitrification; the mode of operation is attributed to a release of carbon disulfide by the compounds.

One additional potential problem which could be presented to the agricultural industry in the very near future, is the loss of the widely used, effective fumigant, 1,2-dibromoethane, due to environmental concerns. This agent is approved for use on the same crops as is carbon disulfide, and is additionally used extensively in chambers for fumigating fruits and vegetables to control various insects.

In view of the above, it is clear that the chemical behavior of the alkaline earth metal thiocarbonate salts is unpredictable. Moreover, it is clear that there is no method taught in the art for preparing either the trithio- or tetrathio-salt of calcium.

A need exists for a fluid which can release carbon disulfide for fumigation and nitrification inhibiting purposes, but which can be stored and handled safely and without significant loss of effectiveness during a reasonable commercial storage and delivery cycle.

It is therefore an object of the present invention to provide a stabilized liquid composition which can be caused to release fumigants, including carbon disulfide.

It is a further object to provide a stabilized composition which is miscible with water to form a fumigant and nitrification inhibitor which can be applied to soils by means of fluid handling equipment or introduced into irrigation water.

Other objects and advantages of the instant invention will be apparent from a careful reading of the specification below.

SUMMARY

The invention is directed to the fumigation of soils, enclosed spaces, agricultural products and other commodities, etc., using compositions which decompose to form carbon disulfide and certain other biocidal materials. Such fumigation can be used to control bacteria, fungi, insects, nematodes, rodents, and weeds, all of which are included herein in the term "pests," and it can be used to inhibit nitrification.

Fumigant compositions are described herein as "thiocarbonates," including, without limitation, salts of trithiocarbonic acid and tetrathiocarbonic acid, compositions having empirical formulae intermediate to these acid salts (such as $MCS_{3.7}$, wherein M is a divalent metal ion), and compositions containing substances in addition to thiocarbonates [such as a stabilized ammonium tetrathiocarbonate which contains ammonium sulfide, i.e., $(NH_4)_2CS_4 \cdot (NH_4)_2S$].

The compositions are generally water soluble and can be prepared, stored, and used in aqueous solutions. Thiocarbonate solutions of the invention are stable during prolonged periods of storage in a closed container, exhibit a low vapor pressure, and are not flammable. For soil fumigation, thiocarbonates can be mixed with fertilizers to provide a multi-functional application.

DETAILED DESCRIPTION

The process of soil fumigation requires the movement of gaseous chemicals through the soil which is treated, and the readily apparent necessity for a sufficient concentration of gas at a given temperature and pressure condition to be lethal to the pest which would be controlled. Volatility of the chemical agent is critical to successful fumigation, since a very volatile substance will disperse too readily and not develop an effective concentration except for locations very close to the point of introduction to the soil. Substances having a very low volatility are also undesirable, since they will not disperse in the soil, and will be effective only at locations near the point of introduction.

Since fumigants typically are effective against a pest only during specific phases in the life cycle of the pest, some measures must be taken to ensure that the fumigant is present during the proper phases. This requirement normally has been met by either applying highly persistent chemicals, applying large enough doses of the chemicals so that the normal decomposition, leaching, volatilization, and other processes will have a lesser effect upon pesticide concentration in the treated environment, or, for highly volatile chemicals, enclosing the treated area (such as by covering soils) for sufficient time to achieve control of the pest. Unfortunately, most of the persistent chemicals are now environmentally undesirable and the noted application methods are sometimes prohibitively expensive.

The term "stability", as used herein, can be regarded as a composite of two concepts: chemical stability and physical stability. Since the effectiveness of a composition depends, at least in part, upon its ability to release carbon disulfide during decomposition, chemical stability is expressed accordingly; this can be quantified by, for example, chemically decomposing the composition at some time and measuring the amount of carbon disulfide which evolves. Alternatively, an indication of the amount of available carbon disulfide can be obtained by spectrophotometrically determining the presence of the thiocarbonyl bond ($>C=S$) in a sample of the composition. The absorbance at wavelengths corresponding to those at which thiocarbonyl is known to absorb energy can be used for a quantitative analysis.

Symptomatic of chemical stability, but having an independent significance, is physical stability. This concept is important due to the nature of the products formed during decomposition of the composition, particularly the ammonia, hydrogen sulfide, and carbon disulfide, which each have a high vapor pressure. It is readily apparent that a change in the physical form of the composition from a solution of low vapor pressure into a mixture of compounds, each possessing a high vapor pressure, imposes some rather stringent requirements upon storage containers. Vapor pressure above the composition of the invention, therefore, will be used herein as an indicator of physical stability; a condition of maintained low vapor pressure is the desired property. Another index of physical instability is the formation of undesirable insoluble precipitates, which frequently comprise sulfur, or of an immiscible liquid phase, such as carbon disulfide. The more general description of physical stability, then, is the maintenance of only a single phase in the composition.

Assessment of the stability of a particular composition must involve consideration of both the chemical stability and the physical stability over a period of time during which stability is desired. Certain formulations do not form precipitates and do not develop high vapor pressures during a reasonable storage period and, therefore, may be preferred over a formulation which has a greater chemical stability, but develops objectionable physical characteristics during storage. As a further example, a composition which is intended to be used as an additive to irrigation water is likely to be selected for its freedom from precipitate formation upon dilution; to obtain this property, a composition having a lower chemical stability could be necessary.

Ammonium thiocarbonate compositions of this invention are normally prepared by mixing the components (ammonia, hydrogen sulfide, carbon disulfide, water, and, optionally, sulfur) in the proper proportions, and under conditions which facilitate removal of the heat generated during the preparation. Most of this heat results from the mixing of ammonia and hydrogen sulfide, and from the addition of carbon disulfide to the other components. No particular order of component addition is required, except that ammonia must either be present prior to hydrogen sulfide addition or must be added concurrently with the hydrogen sulfide. In a typical batch preparation, the required amount of water will be introduced into a container (which has cooling coils or other heat exchanging means), followed by the sequential additions of gaseous or liquid ammonia and hydrogen sulfide, sulfur (if required), and carbon disulfide.

Many variations in the foregoing preparation are possible. For example, ammonia can be added as an aqueous ammonia solution, to satisfy all, or some part, of the ammonia requirement, reducing the amount of cooling needed. A further reduction in cooling can be obtained by using an ammonium sulfide solution or solid to provide any desired amount of the ammonia and hydrogen sulfide requirement. Sulfur, if required, can be added as the element or as a solution in carbon disulfide.

It is possible to replace a portion of the ammonia and hydrogen sulfide with a soluble sulfide material such as alkali metal sulfide, alkaline earth metal sulfide, or any mixture thereof. The maximum replaced portion will usually be equivalent in sulfide content to that amount of hydrogen sulfide which would exceed the carbon disulfide molarity in a particular composition. These alternative compositions are especially useful for soil treatment, when it is desired to incorporate plant nutrients not otherwise present, e.g., potassium and magnesium, for correcting a soil deficiency.

A typical continuous-flow production of the composition includes dissolving molten sulfur in carbon disulfide, using a mixing vessel which can be cooled, for example, by external recycle through a heat exchanger, followed by combining the sulfur solution with water, liquid ammonia and liquid hydrogen sulfide in a cooled reactor vessel.

The reactor in either a batch or continuous process should be maintained at a somewhat elevated temperature, e.g., about 25° C. to about 70° C., to promote the rapid formation of a clear solution. Stirring or other mixing of the reactor contents also is useful in this regard. A holding time of about one hour is normally sufficient for obtaining the desired product solution.

A stabilized fumigant which is obtained by the above preparations comprises an aqueous solution of up to about fifty percent by weight solute, in which solute the molarity of hydrogen sulfide is greater than the molarity of carbon disulfide, and is about one-half the molarity of ammonia, and in which sulfur can also be present. Were it not for the requirement that the hydrogen sulfide molarity exceeds that of the carbon disulfide, the range of solute compositions could include the stoichiometric equivalents of ammonium trithiocarbonate and ammonium tetrathiocarbon- ate. This requirement, in fact, is an important factor in obtaining the enhanced stability exhibited by the compositions of this invention.

One theoretical basis for explaining the enhancement in stability which is obtained by means of the invention can be inferred from the following equations, although we do not intend to be bound by any one particular theory, since other possible explanations could be developed. In the equations, likely equilibrium conditions are indicated by the double arrows, while reactions which are considered to be primarily irreversible are denoted by a single arrow. Equilibration between ammonium tetrathiocarbonate and ammonium trithiocarbonate and its components is represented by (3); a possible decomposition route of ammonium trithiocarbonate into ammonium dithiocarbamate with ammonia and carbon disulfide in an acidic environment is shown by (5); the decomposition of ammonium dithiocarbamate into ammonium thiocyanate is represented by (6).

$$(NH_4)_2CS_4 \rightleftharpoons (NH_4)_2CS_3 + S \tag{2}$$

$$(NH_4)_2CS_3 \rightleftharpoons 2NH_3 + H_2S + CS_2 \tag{3}$$

$$(NH_4)_2CS_3 \rightleftharpoons NH_2CS_2NH_4 + H_2S \tag{4}$$

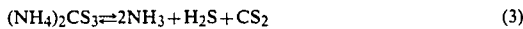

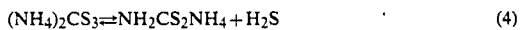

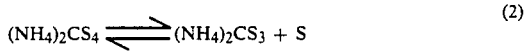

$$NH_2CS_2NH_4 \rightleftharpoons NH_4SCN + H_2S \tag{6}$$

From (2), a prediction can be made that increased stability will result from an excess of elemental sulfur in the composition. This effect has been confirmed.

Using the expression of (3), it can be inferred that an excess of a component will shift the equilibrium to favor maintenance of ammonium trithiocarbonate. This has been disproved in the case of excess carbon disulfide, and also for excess ammonia. The effect of ammonia, however, appears to be expressible as a quadratic function, destabilizing solutions of ammonium trithiocarbonate as the excess ammonia increases, then reversing to provide increasing stability with continued increases in the ammonia level. For excess hydrogen sulfide, however, a stabilizing effect has been found, expressible as a quadratic function to reflect the stabilization as hydrogen sulfide concentration is increased to a particular level, then a decrease in stability for higher levels of hydrogen sulfide.

The reactions of (4) and (6) show a mechanism for the decomposition which results in forming ammonium thiocyanate, thereby destroying the thiocarbonyl bond and preventing the release of carbon disulfide by the composition. According to (5), however, acidic conditions can cause the intermediate product to release carbon disulfide.

Some general parameters which have been determined to effect composition physical stability are as follows for a composition which is an aqueous solution of about 45 percent by weight of a solute comprising hydrogen sulfide, ammonia (at twice the molarity of hydrogen sulfide), carbon disulfide, and sulfur:

(a) the composition is stable for several months without hydrogen sulfide evolution if (1) sulfur molarity is greater than or equal to carbon disulfide molarity, and (2) hydrogen sulfide molarity is less than 1.5 times the carbon disulfide molarity;

(b) for the case described above in (a), carbon disulfide will separate into a separate phase if its molarity is greater than that of hydrogen sulfide; and (c) the composition is stable for several months without sulfur precipitation if (1) sulfur molarity is less than or equal to carbon disulfide molarity, and (2) hydrogen sulfide molarity is equal to or greater than carbon disulfide molarity.

The solubility limit of an ammonium thiocarbonate composition is approximately 50 to 55 percent by weight solute, showing some variability which is dependent upon relative amounts of the various components present. Release of carbon disulfide is rapidly accelerated upon dilution of the composition with water. Some of the possible compositions of the invention, however, are not suitable for uses which require dilution, because of the resulting sulfur precipitation. In general, sulfur precipitation occurs within a few days if (1) hydrogen sulfide molarity (present with approximately twice its molarity of ammonia) is less than about 1.5 times the molarity of carbon disulfide, and (2) sulfur molarity is greater than carbon disulfide molarity, and (3) carbon disulfide is less than about 2.5 percent by weight in the composition.

As a practical matter, the least tolerable manifestation of physical instability is gas evolution, since this causes stresses on the storage container which could result in releasing toxic and flammable or explosive vapors.

The ammonium thiocarbonate compositions are stabilized by excess sulfur against significant increases in vapor pressure, and against significant solid or immiscible liquid phase formation, during reasonable storage periods, and also maintain acceptable chemical stability during such periods.

Alkaline earth metal (i.e., magnesium, calcium, strontium, and barium) thiocarbonates are somewhat more stable against loss of carbon disulfide than is an ammonium thiocarbonate. Moreover, neither alkaline earth metal nor alkali metal (lithium, sodium, potassium and cesium) thiocarbonate solutions form the phytotoxic thiocyanate species upon decomposition, so such solutions generally are more suitable for long-term storage.

Alkaline earth metal thiocarbonates can be prepared by reacting alkaline earth metal sulfides, either alone or mixed with elemental sulfur (when tetrathiocarbonate is to be prepared), with carbon disulfide, preferably in aqueous media, to directly form aqueous fumigant compo- sitions. Alkaline earth metal sulfides can be generated in situ, by reaction of hydrogen sulfide with an aqueous solution or dispersion of alkaline earth metal salts, oxides, hydroxides, and the like. This same procedure is applicable to preparation of alkali metal thiocarbonates.

The preparation is conveniently carried out at temperatures of about 15° C. to about 35° C., but may be conducted between about 0° C. and the boiling point of carbon disulfide, preferably under an inert or reducing gas atmosphere, to avoid oxidation of sulfur compounds to sulfur oxide moieties such as thiosulfates. Reactants are preferably provided in approximately stoichiometric amounts: one mole of alkaline earth metal sulfide per mole of carbon disulfide, to form alkaline earth metal trithiocarbonate, and one additional mole of elemental sulfur added to form alkaline earth metal tetrathiocarbonate. Products have the empirical formula $M_nCS_x$ wherein n is 1 when M is alkaline earth metal, n is 2 when M is alkali metal, and x is 3, 4 or values between 3 and 4.

The solubility limit for alkaline earth metal trithiocarbonates in water is approximately 55 percent by weight; the limit for corresponding tetrathiocarbonates is about 45 percent by weight. Solutions are normally diluted with water to concentrations less than about 33 percent by weight, to avoid precipitation at low temperatures.

Salts may be recovered from the aqueous solutions by evaporation of the water and filtration of the resulting precipitate (under an inert or reducing atmosphere) if it is desirable to store the alkaline earth metal thiocarbonate for extremely long periods prior to use as a fumigant. However, the aqueous solution is substantially stable in and of itself; therefore, there is usually no need to recover the salt as a substantially anhydrous solid. Moreover, it is generally easier to handle the liquid solution than the solid alkaline earth metal thiocarbonate.

While the above-described alkaline earth metal thiocarbonates are the active fumigants and therefore may be used in any form (e.g., as a powder admixed with inert solids, as solution or dispersion in an organic solvent, etc.), it is preferred to use the aqueous solutions directly as fumigants. Therefore, the fumigation method of the invention may be carried out by the application of aqueous solutions of alkaline earth metal thiocarbonates.

The above aqueous reaction solutions may be diluted prior to application to provide a solution concentration of as low as 0.01 percent by weight of the alkaline earth metal thiocarbonate. The aqueous solution may incorporate surfactants to assist in application as a fumigant. Preferably, a strong base, e.g., an alkali metal hydroxide such as sodium hydroxide, is added to the aqueous solution of alkaline earth metal thiocarbonate to increase the stability thereof during application.

The alkaline earth metal thiocarbonates (like the ammonium and alkali metal analogues) decompose upon exposure to the atmosphere, at ambient temperatures and humidities, to yield carbon disulfide. Therefore, the aqueous solution will yield (upon evaporation of the water) a solvated alkaline earth metal thiocarbonate which decomposes to carbon disulfide, in the presence of atmospheric gases at ambient temperatures.

The aqueous solutions of alkaline earth thiocarbonates utilized in the method of this invention are stable against significant increases in vapor pressure, and significant solid phase formation, during storage periods. These solutions also maintain acceptable chemical stability during such periods, as measured by their ability to decompose to carbon disulfide upon application as a fumigant.

Soil application of a thiocarbonate composition can be accomplished either prior to planting or after plant growth is established. It should be noted, however, that different plant species exhibit differing tolerances to chemical agents. In addition, phytotoxicity to a particular plant can be dependent upon its growth stage. Germination is not inhibited for most plant seeds after soil treatment, and growth of established plants is not significantly altered. Some seedlings, though, show phytotoxicity symptoms. Postplant applications of the composition to such diverse crops as corn, cotton, tomatoes, potatoes and grapes have given no indications of phytotoxicity at effective nematocidal application rates, but cucumber plants have been shown to be somewhat sensitive to thiocarbonate.

The compositions can be applied in undiluted form (to minimize the amount which is required per acre) by spraying onto the soil surface, preferably followed within several hours by water application to move the composition into the soil before a significant amount of free carbon disulfide is released. Injection into the soil, using a shank or knife, is also a useful method for applying the compositions. This application can either be "flat," wherein the injectors are closely spaced to treat essentially the entire field area, or can be "localized" by spacing the injectors such that only the plant growing bed is treated, in bands.

Alternatively, those forms of the compositions which are physically stable upon dilution can be mixed into irrigation water and applied by any customary manner, such as through sprinklers, in the water for furrow or flood irrigation, and in drip irrigation systems. The compositions will move into the soil with the water, and decompose to accomplish their fumigation functions, including nitrification inhibition.

Decomposition of the thiocarbonates in the diluted solutions, prior to movement into the soil, can be retarded by increasing the pH of the solutions. With waters having a high total hardness, however, even the inherent alkalinity of thiocarbonate salts can lead to the precipitation of insoluble carbonates, i.e., of calcium, which tend to plug drip irrigation emitters or sprinkler nozzles. Such precipitation can be retarded by the addition of a hardness-complexing agent, such as sodium hexametaphosphate, to the water.

The thiocarbonates can be combined with other agricultural chemicals to provide a multifunctional product. For example, the stable salts may be combined with solid or liquid fertilizers such as urea, ammonia, ammonium nitrate, calcium nitrate, etc. and other sources of plant nutrients. Since the described thiocarbonates inhibit nitrification, they reduce the rate at which ammoniacal compounds, such as fertilizers, are nitrified in the soil. Ammoniacal fertilizers are well known in the art, and as that term is used herein, it includes ammonia and ammonium-containing compounds as well as ammonia and ammonium compound formers such as urea, biuret, etc. Illustrative ammonium-containing compounds include ammonium nitrate, ammonium sulfate, etc.

The compositions also can be used in non-soil fumigation procedures, such as in the chamber fumigation of commodities which are introduced into commerce. In this type of procedure, dilution of a composition or the application of heat, or both, can be used to promote a rapid decomposition into the fumigant components. Upon termination of the fumigation procedure, vapors in the chamber can be drawn through a scrubbing system, e.g., one containing an alkaline aqueous solution, to remove the fumigant and prevent atmospheric pollution when the chamber is opened.

Another important use of the compositions is as a fumigant for stored grains and other agricultural products. If applied to products which are to be stored, a fumigant composition can be applied simply by spraying into the product as it is being transported to the storage enclosure with a conveyor, auger or other device. The composition can be applied to agricultural products which are already in storage, by spraying onto the exposed products and sealing the storage enclosure.

It is also possible to use the thiocarbonate compositions for fumigating rooms or storage enclosures; this is accomplished by spraying the floor and walls with the composition, and sealing the space until the desired fumigation is accomplished. As an alternative to spraying, a technique similar to chamber fumigation can be used, wherein heat decomposes the composition in an enclosed space.

The fumigating ability of compositions described herein has been expressed primarily in terms of the available carbon disulfide content. It should be noted, however, that other components can contribute to efficacy as a fumigant. Ammonia, for example, is a fungicide for use on harvested grapefruit, lemons, oranges, and on grain for feed use. In addition, sulfur is very widely used as a fungicide-acaricide-insecticide, so any of the compositions of the invention which decompose to form sulfur will have similar properties in addition to the properties attributable to the carbon disulfide content.

Upon dilution, acidification, heating or introduction into the soil (which is a form of dilution), the compositions of the invention break down into their components by a process which can be conceptualized as a physical dissociation. In a soil environment, the inorganic cation, sulfur, and hydrogen sulfide components are rapidly withdrawn into soil particles, and thereby rendered more or less immobile, depending upon soil characteristics, moisture, ambient temperature and the like. Certain of these species will be used as plant nutrients. Carbon disulfide, however, is not tightly bound to the soil and readily migrates to perform the fumigation function.

The invention is further described by the following examples which are illustrative of various aspects of the invention, and are not intended as limiting the scope of the invention as defined by the appended claims.

MODES FOR CARRYING OUT THE INVENTION

EXAMPLE 1

Preparation of an ammonium thiocarbonate composition is accomplished, using a 12 liter, three-neck, round-bottom flask, fitted with a sealed stirrer, gas delivery tube, and a U-tube manometer. A 5461 gram charge of water is placed in the flask, and 1266 grams of anhydrous ammonia are added with cooling of the flask and stirring. With further cooling, 1266 grams of hydrogen sulfide are added. To the resulting solution are added 595 grams of finely divided sulfur and, with resumed cooling, 1412 grams of carbon disulfide are also added. Stirring is continued while the mixture is maintained at a temperature between about 24° C. and about 38° C. for a period of about one hour. The resulting clear, deep yellow solution has a composition as follows:

| Component | Weight Percent | Mole Percent |
|---|---|---|
| $NH_3$ | 12.66 | 16.46 |

| Component | Weight Percent | Mole Percent |
|---|---|---|
| $H_2S$ | 12.66 | 8.22 |
| S | 5.95 | 4.11 |
| $CS_2$ | 14.12 | 4.11 |
| $H_2O$ | 54.61 | 67.1 |

This solution has a specific gravity at 21° C. of 1.130, and a crystallization temperature of about −10° C.

EXAMPLE 2

Solutions corresponding in stoichiometry to an ammoniated ammonium trithiocarbonate are prepared by the procedure of Example 1. The chemical stability is determined at 23° C. by measuring absorbance at wavelengths corresponding to those of the thiocarbonyl group (11.0 microns) and the thiocyanate group (4.85 microns) at the time of preparation and at subsequent times, using Fourier-transform infrared spectrophotometry.

When the infrared data are expressed as the result of thiocarbonyl absorbance divided by the sum of thiocarbonyl absorbance plus thiocyanate absorbance (called "absorbance ratio" in this and subsequent examples), a plot can be made versus elapsed time since composition preparation. The natural logarithm of the absorbance ratio is a linear function of elapsed time, so a linear regression by the method of least squares is used to calculate the equation of this line. By solving the equation for an absorbance ratio of one-half of its original value, the "half-life" of the composition is calculated.

Results are obtained as follows:

| Composition, mole percent | | | | Absorbance Ratio | Half-Life, |
|---|---|---|---|---|---|
| $NH_3$ | $H_2S$ | $CS_2$ | $H_2O$ | 0, 2, 4.7 Months | Months |
| 9.93 | 4.14 | 4.13 | 81.80 | 1, 0.45, 0.18 | 2.0 |
| 11.57 | 4.13 | 4.13 | 80.16 | 1, 0.42, 0.16 | 1.9 |
| 13.23 | 4.13 | 4.13 | 78.51 | 1, 0.44, 0.19 | 2.2 |

EXAMPLE 3

The experiment of Example 2 is repeated with solutions containing sulfur and varying amounts of other components, yielding compositions as tabulated:

| Formula Number | Composition, Mole Percent | | | | |
|---|---|---|---|---|---|
| | $NH_3$ | $H_2S$ | $CS_2$ | S | $H_2O$ |
| 1 | 9.38 | 4.69 | 4.70 | 4.70 | 76.53 |
| 2 | 13.06 | 6.53 | 4.76 | 4.77 | 70.88 |
| 3 | 13.32 | 6.66 | 4.86 | 7.42 | 67.74 |
| 4 | 14.52 | 7.26 | 4.79 | 4.79 | 68.64 |
| 5 | 16.47 | 8.23 | 4.11 | 4.11 | 67.07 |
| 6 | 16.80 | 8.40 | 4.18 | 6.73 | 63.89 |

It should be noted that Formula 1 corresponds stoichiometrically to a solution of ammonium tetrathiocarbonate.

Infrared absorption determinations are made using these compositions giving the following calculated half-lives:

| Formula Number | Absorbance Ratio | | | | Half-life, Months |
|---|---|---|---|---|---|
| | 0 Months | 5.5 Months | 12 Months | 15 Months | |
| 1 | 0.95 | 0.63 | 0.62 | 0.37 | 11.9 |
| 2 | 0.96 | 0.74 | 0.66 | 0.53 | 17.7 |
| 3 | 0.96 | 0.80 | 0.72 | 0.62 | 25.8 |
| 4 | 0.96 | 0.78 | 0.67 | 0.37 | 13.1 |
| 5 | 0.96 | 0.67 | 0.58 | 0.48 | 14.2 |
| 6 | 0.95 | 0.70 | 0.60 | 0.48 | 14.8 |

These data show that increasing the content of soluble sulfide enhances chemical stability, and that a further enhancement can be obtained by increasing the sulfur content.

EXAMPLE 4

The compositions of Example 3 are evaluated for physical stability by placing the prepared solutions in a closed container and measuring absolute vapor pressure by flashing the liquid into an evacuated chamber which is connected to an open tube manometer. The following measurements are obtained:

| Formula Number | Absolute Vapor Pressure, mm. Hg | |
|---|---|---|
| | 0 Months | 6 Months |
| 1 | 222 | — |
| 2 | 93 | — |
| 3 | 154 | — |
| 4 | 99 | — |
| 5 | 112 | 274 |
| 6 | 204 | 224 |

All of the formulae have an acceptable vapor pressure at the time of formulation, but the first four formulae each become strongly effervescent during storage, rendering the subsequent vapor pressure measurements unreliable. In addition, an unidentified solid is formed in the container with Formula 1, prior to the six month measurement.

These data demonstrate the enhancement in physical stability which is attributable to an excess of soluble sulfide in the composition.

EXAMPLE 5

Using the procedure of Example 2, chemical stability (in terms of solution half-life) is determined over a period of six months for various compositions prepared according to the method of Example 1. In addition, absolute vapor pressure over the liquid in a closed container is measured at the time of preparing the composition.

Results are as tabulated:

| Composition, Mole Percent | | | | | Half-life, Months | Absolute Vapor Pressure, mm. Hg |
|---|---|---|---|---|---|---|
| $NH_3$ | $H_2S$ | $CS_2$ | S | $H_2O$ | | |
| 9.74 | 4.87 | 4.64 | 4.64 | 76.11 | 13.0 | 254 |
| 11.66 | 4.87 | 4.64 | 4.64 | 74.20 | 9.1 | 102 |
| 13.60 | 4.86 | 4.63 | 4.63 | 72.28 | 7.6 | 81 |
| 15.52 | 4.86 | 4.62 | 4.62 | 70.38 | 6.6 | 80 |
| 10.70 | 5.34 | 4.65 | 4.65 | 74.65 | 11.9 | 209 |
| 12.81 | 5.34 | 4.65 | 4.65 | 72.56 | 10.9 | 83 |
| 14.94 | 5.34 | 4.65 | 4.65 | 70.44 | 7.6 | 80 |
| 17.05 | 5.34 | 4.65 | 4.65 | 68.35 | 7.2 | 87 |
| 10.77 | 5.38 | 4.68 | 5.62 | 73.54 | 17.2 | 323 |
| 12.91 | 5.38 | 4.68 | 5.62 | 71.41 | 11.8 | 92 |
| 15.04 | 5.38 | 4.68 | 5.62 | 69.31 | 7.8 | 73 |
| 17.19 | 5.38 | 4.68 | 5.62 | 67.17 | 7.0 | 90 |
| 10.85 | 5.43 | 4.72 | 6.61 | 72.34 | 17.7 | — |

-continued

| Composition, Mole Percent | | | | | Half-life, | Absolute Vapor |
|---|---|---|---|---|---|---|
| $NH_3$ | $H_2S$ | $CS_2$ | S | $H_2O$ | Months | Pressure, mm. Hg |
| 13.00 | 5.43 | 4.72 | 6.61 | 70.27 | 11.7 | 107 |
| 15.16 | 5.43 | 4.72 | 6.61 | 68.12 | 8.1 | 79 |
| 17.30 | 5.43 | 4.72 | 6.61 | 66.01 | 7.0 | 77 |
| 9.92 | 4.96 | 3.97 | 3.96 | 77.19 | 15.2 | 158 |
| 11.89 | 4.96 | 3.97 | 3.96 | 75.22 | 10.9 | 83 |
| 13.87 | 4.96 | 3.97 | 3.96 | 73.26 | 7.9 | 77 |
| 15.81 | 4.96 | 3.97 | 3.96 | 71.33 | 7.4 | 80 |
| 9.98 | 4.99 | 3.99 | 4.79 | 76.24 | 18.0 | 203 |
| 11.97 | 4.99 | 3.99 | 4.79 | 74.27 | 11.3 | 81 |
| 13.96 | 4.99 | 3.99 | 4.79 | 72.29 | 7.9 | 71 |
| 15.92 | 4.99 | 3.99 | 4.79 | 70.36 | 7.4 | 81 |
| 10.05 | 5.03 | 4.02 | 5.63 | 75.28 | 15.3 | 226 |
| 12.04 | 5.03 | 4.02 | 5.63 | 73.30 | 10.5 | 78 |
| 14.04 | 5.03 | 4.02 | 5.63 | 71.34 | 7.7 | 70 |
| 16.02 | 5.03 | 4.02 | 5.63 | 69.38 | 7.4 | 80 |
| 14.32 | 7.16 | 4.72 | 4.72 | 69.08 | 19.4 | 118 |
| 18.56 | 7.14 | 4.70 | 4.70 | 64.89 | 12.8 | 106 |
| 22.79 | 7.13 | 4.69 | 4.70 | 60.69 | 10.8 | 140 |
| 14.54 | 7.27 | 4.79 | 6.70 | 66.70 | 20.7 | 129 |
| 18.84 | 7.25 | 4.77 | 6.68 | 62.46 | 13.3 | 101 |
| 23.13 | 7.23 | 4.76 | 6.67 | 58.20 | 10.9 | 135 |
| 14.64 | 7.32 | 4.82 | 7.71 | 65.51 | 20.7 | 129 |
| 18.99 | 7.31 | 4.81 | 7.70 | 61.19 | 13.3 | 96 |
| 23.29 | 7.28 | 4.80 | 7.67 | 56.95 | 10.80 | 133 |
| 19.20 | 9.60 | 4.80 | 4.80 | 61.59 | 14.6 | 152 |
| 24.89 | 9.57 | 4.79 | 4.79 | 55.96 | 12.8 | 168 |
| 19.47 | 9.73 | 4.87 | 6.82 | 59.11 | 14.6 | 145 |
| 25.24 | 9.70 | 4.85 | 6.79 | 53.41 | 12.80 | 166 |
| 19.63 | 9.82 | 4.91 | 7.86 | 57.79 | 16.9 | 150 |
| 25.44 | 9.78 | 4.89 | 7.83 | 52.04 | 13.9 | 168 |

Using a multiple linear regression technique, an equation is derived from the data of this example, which can be used to predict the chemical stability of a composition. The equation (7) is as follows, wherein t is the solution half-life (in months) and X is the mole percentage of its subscripted component:

$$t = -34.5 - 2.7\, X_{NH_3} + 0.053\, X_{NH_3}^2 + 16.8\, X_{H_2S} - 0.092\, X_{H_2S}^2 - 2.0\, X_{CS_2} + 0.65\, X_S + 0.21\, X_{H_2O} \quad (7)$$

The data are found to fit this equation quite well, as indicated by the regression correlation of 0.95.

A similar regression calculation is performed, using the vapor pressure data, to predict this physical property of a composition. In the following equation (8), ln(VP) is the natural logarithm of the absolute vapor pressure (millimeters mercury) and X is again the mole percentage of the subscripted component.

$$\ln(VP) = 1.907 - 0.447\, X_{NH_3} + 0.013\, X_{NH_3}^2 + 0.578\, X_{H_2S} - 0.027\, X_{H_2S}^2 + 0.258\, X_{CS_2} + 0.0248\, X_S + 0.040\, X_{H_2O} \quad (8)$$

The fit of data is measured by the correlation of 0.86 which is obtained.

EXAMPLE 6

The rate at which carbon disulfide is lost from diluted ammonium thiocarbonate compositions is determined by bubbling nitrogen through the solutions, and measuring the carbon disulfide content of the gas which leaves the solution, using a mass spectrometer.

In the determination, the solution, corresponding to that of Example 1 (containing 14.1 percent by weight carbon disulfide), is compared to pure carbon disulfide, and to serial dilutions of the Example 1 solution with water, which prepared 10, 1 and 0.1 volume percent solutions of the original composition.

Results are as tabulated, wherein k is the calculated first order rate constant for loss of carbon disulfide, and t is the solution half-life.

| Composition | $k\left(\dfrac{1}{\text{hour}}\right)$ | t (hours) |
|---|---|---|
| $CS_2$ | 2.0 | — |
| Ex. 1, 100% | 0.003 | 230 |
| Ex. 1, 10% | 0.14 | 5.0 |
| Ex. 1, 1% | 1.09 | 0.6 |
| Ex. 1, 0.1% | 1.35 | 0.5 |

It should be noted that the value of k for the 0.1 percent solution is approximately 70 percent of the value obtained for pure carbon disulfide. Similar results are obtained when various dilutions of other thiocarbonate solutions are tested.

EXAMPLE 7

The utility as nematocides for ammonium thiocarbonate compositions is demonstrated in a greenhouse experiment with tomato plants.

In the experiment, eighty containers are used, each containing about 500 grams of sterilized sandy loam soil. Each container is given four 5-milliliter injections of extract from nematode-infested pepper roots, one inch below the soil surface, producing an initial population of 2000 root-knot nematode larvae per container.

Twenty treatments are replicated four times, each treatment consisting of solution injection into the soil at a two inch depth. The treatments include each of the six compositions from Example 3 at three levels, plus one level of the known nematocide 1,2-dibromo-3-chloropropane (DBCP), and a control with only water injected. After injection, each container is enclosed in a plastic bag and placed in the shade for three days. Upon removing the bags, the soils are aerated by stirring, and allowed to stand undisturbed for eight additional days. Following an additional aeration, a tomato seedling is planted in each pot.

Each container receives 25 milligrams nitrogen (as calcium nitrate) immediately after planting, followed by 2 grams of a slow release complete fertilizer. The plants are harvested after 37 days of growth, and soil is removed from the roots by a gentle washing with water. By use of a magnifying glass, the number of root galls is counted on each plant. Roots and tops are then separated by cutting, oven dried at 80° C. and weighed.

Results are as shown in the table, in which the "Application" represents milligrams of treatment per kilogram of soil, calculated as contained carbon disulfide for the Example 3 solution. Gall counts and weights are mean values from the four replicates.

| Treatment | Application, | Gall | Dry Weight, Grams | |
|---|---|---|---|---|
| Solution | ppm | Count | Total | Roots |
| None | — | 24.3 | 1.338 | 0.335 |
| DBCP | 50 | 0* | 1.238 | 0.273 |
| 1 | 22 | 1.3* | 0.933 | 0.175 |
| 1 | 43 | 3.8 | 1.058 | 0.178 |
| 1 | 65 | 1.3* | 0.750 | 0.155 |
| 2 | 22 | 8.3 | 1.323 | 0.298 |
| 2 | 43 | 5.3 | 1.393 | 0.325 |
| 2 | 65 | 5.0 | 1.350 | 0.292 |
| 3 | 22 | 6.5 | 1.135 | 0.253 |
| 3 | 43 | 2.0* | 1.505 | 0.325 |
| 3 | 65 | 4.5 | 1.060 | 0.220 |
| 4 | 22 | 4.5 | 1.145 | 0.243 |

-continued

| Treatment Solution | Application, ppm | Gall Count | Dry Weight, Grams Total | Roots |
|---|---|---|---|---|
| 4 | 43 | 3.3* | 1.458 | 0.303 |
| 4 | 64 | 1.5* | 1.588 | 0.353 |
| 5 | 22 | 7.5 | 1.178 | 0.253 |
| 5 | 43 | 1.0* | 1.930 | 0.415 |
| 5 | 65 | 0.8* | 1.235 | 0.228 |
| 6 | 22 | 6.3 | 1.503 | 0.313 |
| 6 | 43 | 3.5* | 1.688 | 0.368 |
| 6 | 64 | 1.0* | 1.635 | 0.345 |

The gall counts marked by an asterisk are considered to be statistically indistinguishable.

All of the treatments are found to be effective against the nematodes; the degree of control which is provided, as measured by gall counts, apparently is directly dependent upon the application rate, expressed in terms of the carbon disulfide content.

No significant phytotoxicity is observed for the stabilized solutions under conditions shown; strong evidence is seen that Solution 1 (corresponding stoichiometrically to ammonium tetrathiocarbonate) is somewhat phytotoxic at the application rates listed. Further, it should be noted that the stabilized compositions of the invention exhibit a trend toward accelerating tomato plant growth.

EXAMPLE 8

The nematocidal efficacy of ammonium thiocarbonate compositions is demonstrated by application to established grapevines.

In this test, Solutions 1, 2 and 3 from Example 3 are compared with 1,2-dibromo-3-chloropropane (as a commercial emulsifiable concentrate containing 12% DBCP) on grapevines planted seven feet apart, in rows spaced at ten foot intervals. Single vines, replicated six times, are treated with nine soil injections spaced six inches apart in a single four-foot band centered on, and eight inches from, the vine trunk, paralleling the row. Only one side of the vine is treated.

Soil samples at two depths, upper (10 cm. to 30 cm.) and lower (30 cm. to 60 cm.), are taken at locations 15 to 20 cm. outside the band, both immediately before, and 31 days after treatment. These samples are analyzed for the numbers of larvae of various nematode genera.

The table shows results which are obtained. Application Rate is shown as the number of liters per hectare, assuming that the vines would be treated equally on both sides of the row. The line for no treatment represents the injection of only water. All values are for the mean values obtained in the six replicates, calculated as nematode larvae per kilogram of soil.

| Treatment Solution | Application Rate | Nematode Larvae Population, 31 Days | | | | | |
|---|---|---|---|---|---|---|---|
| | | Root-Knot | | Stubby Root | | Dagger | |
| | | Upper | Lower | Upper | Lower | Upper | Lower |
| None | — | 198 | 93 | 5 | 1 | 16 | 6 |
| DBCP | 44 | 3 | 5 | 0 | 0 | 0 | 0 |
| 1 | 560 | 71 | 70 | 0 | 0 | 7 | 0 |
| 1 | 1120 | 42 | 52 | 0 | 0 | 0 | 3 |
| 1 | 1680 | 12 | 31 | 0 | 0 | 0 | 0 |
| 2 | 560 | 84 | 21 | 0 | 0 | 11 | 0 |
| 2 | 1120 | 28 | 17 | 0 | 0 | 2 | 0 |
| 2 | 1680 | 15 | 13 | 0 | 0 | 1 | 0 |
| 3 | 560 | 33 | 33 | 0 | 0 | 2 | 2 |
| 3 | 1120 | 17 | 12 | 0 | 0 | 3 | 0 |
| 3 | 1680 | 12 | 10 | 0 | 0 | 0 | 0 |

The pretreatment nematode counts per kilogram of soil are as follows: Root Knot (*Meloidogyne spp.*) 185 at 10 to 30 cm., 164 at 30 to 60 cm.; Stubby Root (*Trichodorus spp.*) 4 at 10 to 30 cm., 6 at 30 to 60 cm.; Dagger (*Xiphinema spp.*) 50 at 10 to 30 cm., 20 at 30 to 60 cm.

A clear correlation is noted between application rate and nematode population reduction. Also noteworthy is a comparison between Solution 1, corresponding stoichiometrically to ammonium tetrathiocarbonate, and the stabilized compositions of the invention, with regard to the effectiveness at greater soil depths. Since the invention results in stabilization against decomposition, a better movement of active ingredients through the soil can be obtained for a given application rate.

EXAMPLE 9

The ability of ammonium thiocarbonate compositions to combine with nitrogenous chemical fertilizers is demonstrated by dissolving urea in a solution corresponding to that prepared in Example 1, preparing solutions as tabulated:

| Percent Urea (Weight) | Crystallization Temp. (°C.) | Fertilizer Designation | Equivalent $CS_2$ (Wt. %) |
|---|---|---|---|
| 0 | −10 | 10.4-0-0-29.7(S) | 14.1 |
| 10 | −22 | 14.0-0-0-26.8(S) | 12.7 |
| 20 | −36 | 17.6-0-0-21.4(S) | 11.3 |
| 30 | −24 | 21.3-0-0-20.8(S) | 9.9 |
| 40 | −1 | 24.9-0-0-17.8(S) | 8.5 |
| 50 | 26 | 28.5-0-0-13.9(S) | 7.1 |

A minimum crystallization temperature is found at about 20 percent by weight urea, corresponding approximately to a urea-carbon disulfide mole ratio of 2:1. These solutions have stabilities similar to that of stabilized ammonium tetrathiocarbonate solutions, developing slight pressures of hydrogen sulfide over a period of several weeks.

The solutions are useful as providing a means for single application of nitrogen fertilization combined with fumigation.

EXAMPLE 10

Calcium tetrathiocarbonate solution is prepared by mixing 115.8 grams of calcium oxide with 585 grams water, and adding, with vigorous stirring, 71.6 grams of hydrogen sulfide, forming a dark green slurry. When 67.4 grams of sulfur are added, the slurry becomes dark yellow in color; the addition of 180.7 grams of carbon disulfide produces a deep yellow solution which is 36.5 percent by weight calcium tetrathiocarbonate.

EXAMPLE 11

The utility as nematocides for compositions of this invention is demonstrated in a greenhouse experiment with tomato plants.

In the experiment, thirty containers are used, each containing about 500 grams of sterilized sandy loam soil. Each container contains one tomato plant. Each container is injected with four 5-milliliter portions of extract from nematode-infested pepper roots, one inch below the soil surface, producing an initial population of 2000 root-knot nematode larvae (*Meloidogyne incognita*) per container.

Ten treatments are replicated three times, each treatment consisting of drenching the soil with a solution containing the fumigant to provide the dosage of $CS_2$ given in the following table. The solutions are diluted with sufficient water to saturate the soil. The treatments include calcium tetrathiocarbonate, stabilized ammonium tetrathiocarbonate, and carbon disulfide at three levels, plus an untreated control. After drenching, each container is allowed to stand at ambient conditions. The plants are harvested after 30 days of growth, and soil is removed from the roots by a gentle washing with water. By use of a magnifying glass, the number of root galls is counted on each plant.

Results are summarized below, wherein the "Application" represents milligrams of treatment per kilogram of soil, calculated as the thiocarbonate salt and the equivalent carbon disulfide. Gall counts are mean values from the three replicates.

| Composition | Application, ppm Salt[a] | Eq. $CS_2$ | Gall Counts[b] 1 | 2 | 3 | Mean |
|---|---|---|---|---|---|---|
| Control | 0 | 0 | 4 | 7 | 1 | 4.0 |
| $(NH_4)_2CS_4$ $(NH_4)_2S$ | 213 | 30 | 5 | 7 | 3 | 5.0 |
|  | 425 | 60 | 9 | 15 | 6 | 10.0 |
|  | 638 | 89 | 6 | 5 | 2 | 4.3 |
| $CaCS_4$ | 245 | 31 | 16 | 8 | 23 | 15.7 |
|  | 490 | 61 | 11 | 4 | 7 | 7.3 |
|  | 730 | 91 | 3 | 9 | 9 | 7.0 |
| $CS_2$ | — | 32 | 31 | 23 | 12 | 22.0 |
|  | — | 65 | 28 | 19 | 33 | 26.7 |
|  | — | 97 | 27 | 24 | 9 | 20.0 |

[a] $(NH_4)_2CS_4$ $(NH_4)_2S$ applied as a 32.4 percent solution, by weight.
$CaCS_4$ applied as a 29.6 percent solution, by weight.
$CS_2$ applied as the pure liquid.
[b] Number of discrete galls per total root mass.

The calcium tetrathiocarbonate is substantially equivalent to the stabilized ammonium tetrathiocarbonate as a nematocide; however, the calcium thiocarbonates (as well as the other alkaline earth metal thiocarbonates) are found to be less phytotoxic in that they do not form ammonium thiocyanate upon decomposition during storage, nor, unlike the ammonium ion component of the ammonium thoicarbonates, are the individual components of the alkaline earth metal thiocarbonates (i.e., $H_2S$, $S$, $CS_2$, and alkaline earth metal ions) phytotoxic.

EXAMPLE 12

The procedure of Example 11 is repeated except that potassium tetrathiocarbonate is substituted for stabilized ammonium tetrathiocarbonate and an in-vitro nematocidal test is used. In the in-vitro test, the nematode larvae are treated in aqueous suspension for 1 hour at the concentrations of fumigant given in the following table, washed twice with water, and injected into the active root zone of the tomato plants. After thirty days the roots are harvested, examined for galling, giving the results summarized below.

| Control | Gall Count 1 90 | 2 88 | Mean 89 |
|---|---|---|---|
| 50 ppm $CaCS_4$ 6.3 ppm $CS_2$ equiv. | 185 | 149 | 167 |
| 100 ppm $CaCS_4$ 12.5 ppm $CS_2$ equiv. | 132 | 184 | 158 |
| 150 ppm $CaCS_4$ 18.8 ppm $CS_2$ equiv. | 32 | 66 | 49 |
| 50 ppm $K_2CS_4$ 6.5 ppm $CS_2$ equiv. | 33 | 66 | 49.5 |
| 100 ppm $K_2CS_4$ 13 ppm $CS_2$ equiv. | 198 | 145 | 171.5 |
| 150 ppm $K_2CS_4$ 19.5 ppm $CS_2$ equiv. | 49 | 22 | 35.5 |
| 10 ppm $CS_2$ | 64 | 149 | 106.5 |
| 20 ppm $CS_2$ | 29 | 73 | 51.0 |

The results show that the calcium tetrathiocarbonate is substantially equivalent to potassium tetrathiocarbonate as a nematocide. However, as described in the following example, the potassium thiocarbonates are less stable to storage as measured by the loss of their ability to generate the active fumigant carbon disulfide.

EXAMPLE 13

Various tetrathiocarbonate salts are evaluated for storage stability by measuring the loss of the ability of aqueous solutions thereof to generate carbon disulfide upon contact with strong acid. Aqueous solutions of the salts listed in the following table, having an equivalent of from about 14 to about 16 percent by weight carbon disulfide, are stored in air-tight glass containers at a temperature of 49° C. As shown by the data below, the calcium tetrathiocarbonate solution is significantly more stable than the sodium and potassium tetrathiocarbonate solutions and substantially more stable than the ammonium tetrathiocarbonate.

| Cation | Half-life (months) |
|---|---|
| $NH_4^+$ | 0.17 |
| $Na^+$ | 3.0 |
| $K^+$ | 2.9 |
| $Ca^{++}$ | 5.0 |

EXAMPLE 14

Aqueous solutions of alkali metal or alkaline earth metal tri- or tetrathiocarbonates have very high solvency for urea, indicating that eutectic compositions are formed. These combinations are biocidal against bacteria, fungi, nematodes, and insects, while providing a wide range of desirable nitrogen and sulfur fertilizer contents. Furthermore, alkali metal and alkaline earth metal cations, in particular, calcium, magnesium, and potassium, are indispensable plant nutrients. Thus, the compositions described above may be used to provide the major nutrient requirements of crops, while at the same time protecting the crops against pathogens.

To a 41.5 percent, by weight, aqueous solution of calcium tetrathiocarbonate is added urea until the solubility limit of urea is reached. At room temperature, the solution dissolves 122 percent by weight urea. The resulting solution is 55 percent urea, 18.6 percent calcium tetrathiocarbonate, and 26.3 percent water, by weight. Thus, the solvency of the aqueous solution of calcium tetrathiocarbonate for urea is at least as great as that of water alone. Similarly, a 46 percent solution of potassium tetrathiocarbonate dissolves 100 percent of its own weight of urea. Similar results are obtained with other tri- and tetrathiocarbonates of alkali metal and alkaline earth metals.

EXAMPLE 15

It has been found that the stability of dilute aqueous solutions of alkaline earth metal thiocarbonates (as measured by rate of decomposition to yield carbon disulfide) increases with the pH of the solution. Therefore, in irrigation applications, wherein dilute solutions are utilized, it is desirable to provide a base to increase the pH of the irrigation solution. A suitable base may be selected from the group consisting of the alkali metal hydroxides and carbonates, e.g. KOH, NaOH, $K_2CO_3$, $Na_2CO_3$, etc. The base may be added to the water of dilution utilized in making up the irrigation solution or can be incorporated in the aqueous alkaline earth metal thiocarbonate solution. Sufficient base is added to provide an irrigation solution having a pH of at least about 7 and preferably at least about 8. Most preferably, the amount of base added will provide an irrigation solution having a pH of at least about 9.

To demonstrate the effect of pH on evaporative losses of $CS_2$ from thiocarbonates, solutions are injected into a closed bottle containing well stirred citratephosphate buffers, giving a solution concentration of 125 milligrams per liter of thiocarbonate ion. Pure carbon disulfide is also injected, for comparison. A syringe is used to periodically sample air in the bottle, and the air is analyzed by gas chromatography. Half-life times for production of carbon disulfide are summarized in the following table.

| pH | Half-life (minutes) | | |
|---|---|---|---|
| | $CS_2$ | $(NH_4)_2CS_4$ $(NH_4)_2S$ | $CaCS_4$ |
| 5.2 | 1 | 1 | 1 |
| 6.0 | 1 | 1 | 1.8 |
| 7.0 | 1 | 2.1 | 2.7 |
| 8.0 | 1 | 9.2 | 8.0 |
| 9.0 | — | 26.1 | 11.3 |

Results for calcium tetrathiocarbonate at pH values above 7 in this buffer system are unreliable, since calcium phosphates tend to precipitate, causing more rapid dissociation of the thiocarbonate. It is apparent, however, that decomposition for these two compounds proceeds at similar rates.

EXAMPLE 16

Thiocarbonate solutions are used in a test of their fungicidal properties. Cultures of four plant pathogenic fungi are grown upon potato dextrose agar at room temperature, in diffuse natural lighting. After one week, square blocks having 2 millimeter sides are cut from the edges of actively growing mycelia spots on the agar.

The blocks are immersed in sterile deionized water, as a control, or in dilutions of thiocarbonate solutions using the sterile water, in a closed container. Subsequently, the blocks are removed and placed upon agar in clean plates, and mycelia are allowed to grow for one week.

Radial growth of mycelia colonies is measured for each of the six to eight replicate plates used for a particular fungus, and average colony radius is calculated. Percent control is defined by the following equation:

$$\text{Percent control} = 1 - \left(\frac{\text{Average radius of treated plates}}{\text{Average radius of control plates}}\right) \times 100$$

Results are summarized in the table which follows. Concentrations given for solutions used to treat the agar blocks are expressed in grams of thiocarbonate solution per liter of diluted solution. These results show that the compositions have activity against fungi.

| Treatment | g/l | Percent Control | | | |
|---|---|---|---|---|---|
| | | Fusarium oxysporum | Phytophthora cinnamomi | Verticillium dahliae | Sclerotium rolfsii |
| $K_2CS_4$ | 100 | 76 | 100 | 100 | 100 |
| (9.43% $CS_2$) | 10 | 10 | 68 | 15 | 8 |
| | 1 | 8 | 56 | 27 | 42 |
| $K_2CS_4$ | 100 | 74 | 100 | 100 | 100 |
| +6.1% $NH_3$ | 10 | 83 | 100 | 41 | 59 |
| (8.21% $CS_2$) | 1 | 87 | 100 | 46 | 45 |
| $K_2CS_4$ | 100 | 92 | 100 | 100 | 100 |
| +10.7% urea | 10 | 6 | 97 | 53 | 100 |
| (8.17% $CS_2$) | 1 | 0 | 30 | 77 | 48 |
| $Na_2CS_4$ | 100 | 100 | 100 | 100 | 100 |
| (10.6% $CS_2$) | 10 | 6 | 37 | 26 | 100 |
| | 1 | 4 | 37 | 23 | 54 |
| $Na_2CS_4$ | 100 | 100 | 100 | 100 | 100 |
| +6.1% $NH_3$ | 10 | 14 | —* | 59 | 100 |
| (9.52% $CS_2$) | 1 | 2 | —* | 37 | 48 |
| $Na_2CS_4$ | 100 | 94 | 100 | 100 | 100 |
| +10.7% urea | 10 | 30 | —* | 20 | 100 |
| (9.69% $CS_2$) | 1 | 8 | —* | 8 | 50 |
| $CaCS_4$ | 100 | 100 | 100 | 100 | 100 |
| (2.8% $CS_2$) | 10 | 18 | 56 | 22 | 62 |
| | 1 | 3 | 56 | 13 | 46 |
| $(NH_4)_2CS_4$ | 100 | 100 | 100 | 91 | 100 |
| $(NH_4)_2S$ | 10 | 100 | 74 | 81 | 93 |
| (13.0% $CS_2$) | 1 | 70 | 97 | 41 | 49 |

*contaminated cultures

EXAMPLE 17

The effect of various application rates of thiocarbonates for pest control is shown in a series of experiments.

Citrus trees are treated with a 32 percent by weight solution of $(NH_4)_2CS_4 \cdot (NH_4)_2S$ applied evenly to soil around the trunks using a sprinkler can, and thoroughly watered in with flood irrigation. Soil samples taken 30 days following treatment are counted for citrus nematode larvae, giving results summarized below, where the application rate is expressed in liters per hectare.

| Application | Larvae/500 cc. |
|---|---|
| 0 | 2887 |
| 470 | 325 |
| 940 | 521 |
| 1870 | 1739 |

EXAMPLE 18

Using a drip irrigation system, grapevines are treated with $(NH_4)_2CS_4 \cdot (NH_4)_2S$ at a rate of about 43 kilograms per hectare, using three equal treatment applications made at three day intervals. Total control of citrus nematode larvae is obtained over a three month period.

EXAMPLE 19

In a laboratory test, it is found that a single application of the composition described in Example 18 produces 96 to 100 percent control of the citrus nematode larvae at an application rate of about 655 kilograms per hectare.

EXAMPLE 20

Sugar beets, infested with sugar beet cyst nematodes (*Heterodera spp.*), are treated by application to the soil of about 94 kilograms per hectare of $CaCS_4$, dissolved in irrigation water. Counts of nematode larvae in the soil, following treatment, remained high, but the larvae were not viable, due to parasitism by other soil organisms.

EXAMPLE 21

In petri dish tests of $CaCS_4$ against the fungus *Fusarium spp.*, control with solutions containing less than about 10 grams per liter of the compound, in both potato dextrose agar and potato dextrose broth, is obtained using the solution when the broth also contains another fungus, *Trichoderma spp.*

The results of Examples 17 through 21 indicate that control of soil-borne plant parasites can be obtained by applying sub-lethal doses of biocide, that is, amounts which are insufficient to substantially eradicate the pests, but which can weaken the pests and thereby facilitate their control by natural predators in the soil. Decreased long-term control is obtained by higher application rates of biocide, since the higher rates can stimulate an increase in the reproductive effort of an organism; a better initial kill will be followed by, for example, a much larger egg hatch, yielding an actual net increase in parasite population. Very high application rates will effectively eradicate susceptible pests, but may lead to rapid proliferation of less susceptible pests, which may also be undesirable.

Another useful application method initially utilizes only sufficient pesticide to stimulate a large reproductive effort, followed by a high dosage, immediately after the egg hatch, to obtain a maximum pest mortality.

EXAMPLE 22

The effect of multiple applications of lethal doses of thiocarbonates is shown in a series of experiments. In the experiments, two or more small, but lethal, doses are applied to the soil repetitively, beginning at a time predicted to correspond to a seasonal increase in population of a susceptible phase in the life cycle of a pathogen. Such application permits the use of minimum quantities of non-persistent pesticides. In the experiments, the thiocarbonate is a 32 percent by weight solution of $(NH_4)_2CS_4 \cdot (NH_4)_2S$.

Soil systems, containing all life stages of reniform nematode and used for pineapple crops with drip irrigation, are treated with thiocarbonate solution. One soil receives only a single preplant treatment. Another area receives the same quantity of thiocarbonate, but applied with the irrigation water in six monthly doses (one-sixth before planting and the remainder in five equal doses). A third area receives no treatment. Soil samples are taken at fixed intervals following the first treatment and counts made of nematodes per 300 milliliters of soil. Results are summarized in the following table for tests at two treatment levels.

| Time, Months | Nematode Counts | | |
|---|---|---|---|
| | Preplant | Monthly | Untreated |
| Trial A - total 280 liters per hectare | | | |
| 0.5 | 63 | 73 | 150 |
| 1 | 50 | 23 | 104 |
| 2 | 164 | 47 | 128 |
| 3 | 67 | 15 | 88 |
| 4 | 340 | 228 | 59 |
| 5 | 248 | 101 | 136 |
| Trial B - total 560 liters per hectare | | | |
| 0.5 | 50 | 176 | 150 |
| 1 | 51 | 54 | 104 |
| 2 | 61 | 28 | 128 |
| 3 | 68 | 28 | 88 |
| 4 | 1972 | 64 | 59 |
| 5 | 713 | 158 | 136 |

Grape vines are treated with monthly applications of thiocarbonate, at a rate of 190 liters per hectare, applied in furrow irrigation water. Soil samples, taken after the first treatment and at monthly intervals thereafter, are counted for root-knot nematode, giving results summarized in the following table:

| Time, Months | Nematode Counts per Kg. Soil | |
|---|---|---|
| | Treated Soil | Untreated Soil |
| 0 | 265 | 350 |
| 1 | 68 | 135 |
| 2 | 30 | 110 |
| 3 | 7.5 | 36 |
| 4 | 77 | 95 |
| 5 | 270 | 460 |

Soil used for growing potatoes, and known to contain several active bacterial and fungal plant pathogens, but no significant nematode population, is treated with thiocarbonate solution. The following table summarizes results of the experiment. In the table, the treatment on 25 May is before planting. Yield is shown in metric tons per hectare, for both the total potato harvest and those potatoes of the largest size (U.S. Number 1). When no treatment is given to a particular plot, a urea-ammonium nitrate fertilizer solution is applied, in an amount which will provide a total amount of nitrogen equivalent to ammonium ion in the fumigant applied to other plots.

| Liters per Hectare Applied | | | Yield | |
|---|---|---|---|---|
| 25 May | 7 July | 15 August | No. 1. | Total |
| 374 | 374 | 374 | 14.2 | 38.1 |
| 1122 | 0 | 0 | 14.1 | 33.2 |
| 748 | 0 | 374 | 19.4 | 38.8 |
| 0 | 748 | 374 | 20.1 | 42.4 |
| 0 | 374 | 748 | 26.8 | 50.8 |
| 0 | 0 | 0 | 13.1 | 31.5 |

EXAMPLE 23

Experiments are performed to demonstrate the advantages of applying thiocarbonates to moist soils.

A sandy loam soil is placed in 1-liter glass bottles, fitted with stoppers having fluorocarbon liners and silicone rubber septa, to give a soil depth of about 4 cm. Water is added to the soil, in quantities to obtain 50 and 100 percent soil saturation. Thiocarbonate solution or carbon disulfide is injected near the bottom of the soil layer, the bottles are promptly sealed, and the air space in the bottles is sampled at intervals with a syringe, for gas chromatographic analysis of $CS_2$. Results are summarized below, wherein degradation time is the number of hours required to achieve the maximum $CS_2$ concentration in the air space.

| Soil Moisture % of Saturation | Compound | Degradation Time, hours |
|---|---|---|
| 0 | $CS_2$ | 3.5 |
| | $(NH_4)_2CS_4$ $(NH_4)_2S$ | 2 |
| | $K_2CS_4$ | 2 |
| | $CaCS_4$ | 4 |
| 50 | $CS_2$ | 3.5 |
| | $(NH_4)_2CS_4$ $(NH_4)_2S$ | 3 |
| | $K_2CS_4$ | 5 |
| | $CaCS_4$ | 5 |
| 100 | $CS_2$ | 3.5 |
| | $(NH_4)_2CS_4$ $(NH_4)_2S$ | 48 |
| | $K_2CS_4$ | 48 |
| | $CaCS_4$ | 48 |

EXAMPLE 24

The ability of the described thiocarbonate compounds to inhibit nitrification of ammoniacal fertilizers in soil can be illustrated by applying to two separate plots of sandy loam soil a urea solution in irrigation water at a rate corresponding to 200 lbs. urea per acre with sufficient water to increase the soil water content to at least 50 percent. This application can be followed, on one of the plots treated with the urea solution and within one hour of application of the urea solution, with application of an aqueous solution containing 5 weight percent calcium tetrathiocarbonate applied at a rate of 100 liters per acre in sufficient irrigation water to increase the soil water content to 100 percent of saturation. The urea in the soil treated with the calcium tetrathiocarbonate solution will be nitrified more slowly than is the urea in the plot not treated with the thiocarbonate.

While particular embodiments of the invention have been described, it will be understood, of course, that the invention is not limited thereto, since many obvious modifications can be made, and it is intended to include within this invention any such modifications as will fall within the scope of the appended claims.

Having now described the invention, we claim:

1. A method for inhibiting the nitrification of an ammoniacal fertilizer in soil comprising introducing into soil containing said ammoniacal fertilizer (a) an amount of water sufficient to obtain a soil water content greater than 50 percent of soil saturation and to substantially retard the decomposition rate of the thiocarbonate compound hereinafter defined relative to the decomposition rate of said compound at 50 percent of soil saturation, and (b) a soil fumigation effective amount of an aqueous solution of a thiocarbonate compound of ammonium, lithium, sodium, potassium, cesium, magnesium, calcium, strontium, or barium ions, or mixtures of two or more of such compounds.

2. A method for fertilizing soil comprising introducing into said soil an ammoniacal fertilizer selected from the group consisting of urea, ammonium compounds, and combinations thereof and a thiocarbonate compound of ammonium, lithium, sodium, potassium, cesium, magnesium, calcium, strontium, or barium ions, or mixtures of two or more of such compounds, wherein said soil contains, or is moistened during application of said thiocarbonate compound to contain, sufficient water to obtain a moisture content in excess of 50 percent of the soil saturation level and sufficient to substantially retard the decomposition rate of said thiocarbonate compound relative to its decomposition rate at a moisture content of 50 percent of soil saturation.

3. A soil fumigation method comprising introducing into said soil an ammoniacal fertilizer and a compound selected from the group consisting of alkali metal and alkaline earth metal thiocarbonate compounds and combinations thereof, wherein said soil contains, or is moistened during application of said compound to contain, a moisture level corresponding to about 100 percent soil saturation.

4. The method defined in claims 1 or 2 wherein the soil is moistened to contain about 100 percent of an amount of water which will saturate the soil.

5. The method defined in claims 1, 2 or 3 wherein the pH of said solution is greater than about 7.

6. The method defined in claims 1, 2 or 3 wherein the pH of said solution is greater than about 8.

7. The method defined in claims 1, 2 or 3 wherein said compound is mixed with irrigation water and is applied to said soil with said irrigation water.

8. The method defined in claims 1, 2 or 3 wherein the pH of said solution is about 9 or greater.

9. The method defined in claims 1, 2 or 3 wherein said thiocarbonate compound comprises a member selected from the group consisting of alkali and alkaline earth metal tetrathiocarbonates and combinations thereof.

10. The method defined in claims 1, 2 or 3 wherein said thiocarbonate compound comprises an alkaline earth tetrathiocarbonate.

11. The method defined in claims 1 or 3 wherein said ammoniacal fertilizer is selected from the group consisting of ammonia, ammonium compounds other than said thiocarbonate, urea, biuret, and combinations thereof.

12. The method defined in claims 1, 2 or 3 wherein said thiocarbonate compound has an empirical formula approximating $M_nCS_x$, wherein M is an alkaline earth metal or an alkali metal, n is 1 when M is an alkaline earth metal, n is 2 when M is an alkali metal, and x is 3, 4, or values between 3 and 4.

13. The method defined in claim 1 wherein said thiocarbonate compound comprises ammonia, hydrogen sulfide, and carbon disulfide, wherein the molarity of hydrogen sulfide is greater than the molarity of carbon disulfide, and is about one-half the molarity of ammonia.

14. The method defined in claim 13 wherein said compound further comprises sulfur in an amount up to about twice the molarity of carbon disulfide.

15. The method defined in claim 1 wherein said compound is introduced into said soil with said water.

16. The method defined in claims 1, 2 or 3 wherein said soil is moistened with water, and said compound is then introduced into the moistened soil as a solution with irrigation water.

* * * * *

UNITED STATES PATENT AND TRADEMARK OFFICE
CERTIFICATE OF CORRECTION

PATENT NO. : 5,022,912

DATED : June 11, 1991

INVENTOR(S) : Donald C. Young and James A. Green, II

It is certified that error appears in the above-identified patent and that said Letters Patent is hereby corrected as shown below:

On the title page item [56] should read;

In References Cited, reference number "4,042,501" should be -- 1,042,501 --.

In Abstract, second paragraph, line 5, "acids" should be -- acid --.

Signed and Sealed this

First Day of December, 1992

Attest:

DOUGLAS B. COMER

*Attesting Officer*     *Acting Commissioner of Patents and Trademarks*